(12) United States Patent
Guo et al.

(10) Patent No.: US 12,110,497 B2
(45) Date of Patent: Oct. 8, 2024

(54) PSEUDOTYPED INSECT BACULOVIRUS GENE TRANSFER SYSTEM AND PSEUDOTYPED BACULOVIRUS FOR SHRIMPS, CONSTRUCTION METHOD AND USE THEREOF

(71) Applicant: Ocean University of China, Shandong (CN)

(72) Inventors: Huarong Guo, Shandong (CN); Mengxi Wu, Shandong (CN)

(73) Assignee: OCEAN UNIVERSITY OF CHINA, Shandong (CN)

( * ) Notice: Subject to any disclaimer, the term of this patent is extended or adjusted under 35 U.S.C. 154(b) by 621 days.

(21) Appl. No.: 16/997,231

(22) Filed: Aug. 19, 2020

(65) Prior Publication Data

US 2021/0292787 A1 Sep. 23, 2021

(30) Foreign Application Priority Data

Mar. 19, 2020 (CN) .......................... 202010196617.0

(51) Int. Cl.
*C12N 15/86* (2006.01)
*C12N 7/00* (2006.01)

(52) U.S. Cl.
CPC ............... *C12N 15/86* (2013.01); *C12N 7/00* (2013.01); *C12N 2710/14043* (2013.01); *C12N 2800/105* (2013.01)

(58) Field of Classification Search
CPC .......... C12N 15/86; C12N 2710/14043; C12N 2800/105; C07K 14/005
See application file for complete search history.

(56) References Cited

PUBLICATIONS

Syed MS, Kwang J. Oral vaccination of baculovirus-expressed VP28 displays enhanced protection against White Spot Syndrome Virus in Penaeus monodon. PLoS One. 2011;6(11):e26428. (Year: 2011).*

Hitchman RB, Possee RD, King LA. Baculovirus expression systems for recombinant protein production in insect cells. Recent Pat Biotechnol. 2009;3(1):46-54. (Year: 2009).*

Longjun Pu, Jing Wang, Xiaojuan Zhang, Huarong Guo. Development of pseudotyped retroviral system for effective gene transfer and expression in penaeid shrimp cells. Aquaculture. vol. 467, Jan. 20, 2017, pp. 198-210. (Year: 2017).*

* cited by examiner

*Primary Examiner* — Nicole Kinsey White
*Assistant Examiner* — Ruixue Wang
(74) *Attorney, Agent, or Firm* — Buckley, Maschoff & Talwalkar LLC

(57) ABSTRACT

The present invention relates to a pseudotyped insect baculovirus gene transfer system and a virus for shrimps, and a construction method and use thereof. The present invention belongs to the technical field of genetic engineering. The pseudotyped insect baculovirus gene transfer system for shrimps disclosed in the present invention includes a Bac-to-Bac insect baculovirus expression system, an expression plasmid carrying shrimp virus envelope protein gene and an insect packaging cell. The present invention can achieve stable and efficient transfer and expression of a foreign gene in a shrimp tissue and cell.

4 Claims, 9 Drawing Sheets
Specification includes a Sequence Listing.

SEQUENCE LISTING

```
<160> NUMBER OF SEQ ID NOS: 8

<210> SEQ ID NO 1
<211> LENGTH: 625
<212> TYPE: DNA
<213> ORGANISM: artificial sequence
<220> FEATURE:
<223> OTHER INFORMATION: the nucleotide sequence of the plasmid

<400> SEQUENCE: 1
attgccacca tggatctttc tttcactctt tcggtcgtgt cggccatcct cgccatcact     60
gctgtgattg ctgtatttat tgtgattttt aggtatcaca acactgtgac caagaccatc    120
gaaacccaca caggcaatat cgagacaaac atggatgaaa acctccgcat tcctgtgact    180
gctgaggttg gatcaggcta cttcaagatg actgatgtgt cctttgacag cgacaccttg    240
ggcaaaatca agatccgcaa tggaaagtct gatgcacaga tgaaggaaga agatgcggat    300
cttgtcatca ctcccgtgga gggccgagca ctcgaagtga ctgtggggca gaatctcacc    360
tttgagggaa cattcaaggt gtggaacaac acatcaagaa agatcaacat cactggtatg    420
cagatggtgc caaagattaa cccatcaaag gcctttgtcg gtagctccaa cacctcctcc    480
ttcacccccg tctctattga tgaggatgaa gttggcacct ttgtgtgtgg taccaccttt    540
ggcgcaccaa ttgcagctac cgccggtgga aatcttttcg acatgtacgt gcacgtcacc    600
tactctggca ctgagaccga gtaag                                          625

<210> SEQ ID NO 2
<211> LENGTH: 204
<212> TYPE: PRT
<213> ORGANISM: artificial sequence
<220> FEATURE:
<223> OTHER INFORMATION: the amino acid sequence of the plasmid

<400> SEQUENCE: 2

Met Asp Leu Ser Phe Thr Leu Ser Val Val Ser Ala Ile Leu Ala Ile
1               5                   10                  15

Thr Ala Val Ile Ala Val Phe Ile Val Ile Phe Arg Tyr His Asn Thr
            20                  25                  30

Val Thr Lys Thr Ile Glu Thr His Thr Gly Asn Ile Glu Thr Asn Met
        35                  40                  45

Asp Glu Asn Leu Arg Ile Pro Val Thr Ala Glu Val Gly Ser Gly Tyr
    50                  55                  60

Phe Lys Met Thr Asp Val Ser Phe Asp Ser Asp Thr Leu Gly Lys Ile
65                  70                  75                  80
```

Lys Ile Arg Asn Gly Lys Ser Asp Ala Gln Met Lys Glu Glu Asp Ala
                85                  90                  95

Asp Leu Val Ile Thr Pro Val Glu Gly Arg Ala Leu Glu Val Thr Val
            100                 105                 110

Gly Gln Asn Leu Thr Phe Glu Gly Thr Phe Lys Val Trp Asn Asn Thr
        115                 120                 125

Ser Arg Lys Ile Asn Ile Thr Gly Met Gln Met Val Pro Lys Ile Asn
130                 135                 140

Pro Ser Lys Ala Phe Val Gly Ser Ser Asn Thr Ser Ser Phe Thr Pro
145                 150                 155                 160

Val Ser Ile Asp Glu Asp Glu Val Gly Thr Phe Val Cys Gly Thr Thr
                165                 170                 175

Phe Gly Ala Pro Ile Ala Ala Thr Ala Gly Gly Asn Leu Phe Asp Met
            180                 185                 190

Tyr Val His Val Thr Tyr Ser Gly Thr Glu Thr Glu
        195                 200

<210> SEQ ID NO 3
<211> LENGTH: 1809
<212> TYPE: DNA
<213> ORGANISM: artificial sequence
<220> FEATURE:
<223> OTHER INFORMATION: the nucleotide sequence of the GUS reporter
      gene

<400> SEQUENCE: 3
atggtccgtc ctgtagaaac cccaacccgt gaaatcaaaa aactcgacgg cctgtgggca      60
ttcagtctgg atcgcgaaaa ctgtggaatt gatcagcgtt ggtgggaaag cgcgttacaa     120
gaaagccggg caattgctgt gccaggcagt tttaacgatc agttcgccga tgcagatatt     180
cgtaattatg cgggcaacgt ctggtatcag cgcgaagtct ttataccgaa aggttgggca     240
ggccagcgta tcgtgctgcg tttcgatgcg gtcactcatt acggcaaagt gtgggtcaat     300
aatcaggaag tgatggagca tcagggcggc tatacgccat ttgaagccga tgtcacgccg     360
tatgttattg ccgggaaaag tgtacgtatc accgtttgtg tgaacaacga actgaactgg     420
cagactatcc cgccgggaat ggtgattacc gacgaaaacg gcaagaaaaa gcagtcttat     480
tccatgattt cttttaactat gccggaatcc atcgcagcgt aatgctctac caccgccga     540 acacctgggt ggacgatatc accgtggtga cgcatgtcgc gcaagactgt aaccacgcgt     600
ctgttgactg gcaggtggtg gccaatggtg atgtcagcgt tgaactgcgt gatgcggatc     660
aacaggtggt tgcaactgga caaggcacta gcgggacttt gcaagtggtg aatccgcacc     720
tctggcaacc gggtgaaggt tatctctatg aactgtgcgt cacagccaaa gccagacag     780 agtgtgatat ctaccgcgct tcgcgtcggca tccggtcagt ggcagtgaag gcgaacagt     840 tcctgattaa ccacaaaccg ttctacttta ctggctttgg tcgtcatgaa gatgcggact     900
tacgtggcaa aggattcgat aacgtgctga tggtgcacga ccacgcatta atggactgga     960
ttggggccaa ctcctaccgt acctcgcatt acccttacgc tgaagagatg ctcgactggg    1020
cagatgaaca tggcatcgtg gtgattgatg aaactgctgc tgtcggcttt aacctctctt    1080
taggcattgg tttcgaagcg ggcaacaagc cgaaagaact gtacagcgaa gaggcagtca    1140
acggggaaac tcagcaagcg cacttacagg cgattaaaga gctgatagcg cgtgacaaaa    1200
accacccaag cgtggtgatg tggagtattg ccaacgaacc ggataccgt ccgcaaggtg    1260 cacgggaata tttcgcgcca ctggcggaag caacgcgtaa actcgacccg acgcgtccga    1320

```
tcacctgcgt caatgtaatg ttctgcgacg ctcacaccga taccatcagc gatctctttg    1380
atgtgctgtg cctgaaccgt tattacggat ggtatgtcca agcggcgat ttggaaacgg    1440 cagagaaggt actggaaaaa gaacttctgg cctggcagga gaaactgcat cagccgatta    1500
tcatcaccga atacggcgtg gatacgttag ccgggctgca ctcaatgtac accgacatgt    1560
ggagtgaaga gtatcagtgt gcatggctgg atatgtatca ccgcgtcttt atcgcgtcag    1620
cgccgtcgtc ggtgaacagg tatggaattt cgccgatttt gcgacctcgc aaggcatatt    1680
gcgcgttggc ggtacaagaa agggatcttc actcgcgacc gcaaaccgaa gtcggcggct    1740
tttctgctgc aaaaacgctg gactggcatg aacttcggtg aaaaaccgca gcagggaggc    1800
aaacaatga                                                            1809
```

<210> SEQ ID NO 4
<211> LENGTH: 586
<212> TYPE: PRT
<213> ORGANISM: artificial sequence
<220> FEATURE:
<223> OTHER INFORMATION: the amino acid sequence of a protein
      corresponding to the GUS reporter gene

<400> SEQUENCE: 4

```
Met Val Arg Pro Val Glu Thr Pro Thr Arg Glu Ile Lys Lys Leu Asp
1               5                   10                  15

Gly Leu Trp Ala Phe Ser Leu Asp Arg Glu Asn Cys Gly Ile Asp Gln
            20                  25                  30

Arg Trp Trp Glu Ser Ala Leu Gln Glu Ser Arg Ala Ile Ala Val Pro
        35                  40                  45

Gly Ser Phe Asn Asp Gln Phe Ala Asp Ala Asp Ile Arg Asn Tyr Ala
    50                  55                  60

Gly Asn Val Trp Tyr Gln Arg Glu Val Phe Ile Pro Lys Gly Trp Ala
65                  70                  75                  80

Gly Gln Arg Ile Val Leu Arg Phe Asp Ala Val Thr His Tyr Gly Lys
                85                  90                  95

Val Trp Val Asn Asn Gln Glu Val Met Glu His Gln Gly Gly Tyr Thr
            100                 105                 110

Pro Phe Glu Ala Asp Val Thr Pro Tyr Val Ile Ala Gly Lys Ser Val
        115                 120                 125

Arg Ile Thr Val Cys Val Asn Asn Glu Leu Asn Trp Gln Thr Ile Pro
    130                 135                 140

Pro Gly Met Val Ile Thr Asp Glu Asn Gly Lys Lys Lys Gln Ser Tyr
145                 150                 155                 160

Ser Met Ile Ser Leu Thr Met Pro Glu Ser Ile Ala Ala Cys Ser Thr
                165                 170                 175

Pro Arg Arg Thr Pro Gly Trp Thr Ile Ser Pro Trp Arg Met Ser Arg
            180                 185                 190

Lys Thr Val Thr Thr Arg Leu Leu Thr Gly Arg Trp Trp Pro Met Val
        195                 200                 205

Met Ser Ala Leu Asn Cys Val Met Arg Ile Asn Arg Trp Leu Gln Leu
    210                 215                 220

Asp Lys Ala Leu Ala Gly Leu Cys Lys Trp Ile Arg Thr Ser Gly Asn
225                 230                 235                 240

Arg Val Lys Val Ile Ser Met Asn Cys Ala Ser Gln Pro Lys Ala Arg
                245                 250                 255

Gln Ser Val Ile Ser Thr Arg Phe Ala Ser Ala Ser Gly Gln Trp Gln
```

```
            260                 265                 270
Arg Ala Asn Ser Ser Leu Thr Thr Asn Arg Ser Thr Leu Leu Ala Leu
            275                 280                 285

Val Val Met Lys Met Arg Thr Tyr Val Ala Lys Asp Ser Ile Thr Cys
    290                 295                 300

Trp Cys Thr Thr Thr His Trp Thr Gly Leu Gly Pro Thr Pro Thr Val
305                 310                 315                 320

Pro Arg Ile Thr Leu Thr Leu Lys Arg Cys Ser Thr Gly Gln Met Asn
                325                 330                 335

Met Ala Ser Trp Leu Met Lys Leu Leu Leu Ser Ala Leu Thr Ser Leu
            340                 345                 350

Ala Leu Val Ser Lys Arg Ala Thr Ser Arg Lys Asn Cys Thr Ala Lys
                355                 360                 365

Arg Gln Ser Thr Gly Lys Leu Ser Lys Arg Thr Tyr Arg Arg Leu Lys
            370                 375                 380

Ser Arg Val Thr Lys Thr Thr Gln Ala Trp Cys Gly Val Leu Pro Thr
385                 390                 395                 400

Asn Arg Ile Pro Val Arg Lys Val His Gly Asn Ile Ser Arg His Trp
                405                 410                 415

Arg Lys Gln Arg Val Asn Ser Thr Arg Arg Val Arg Ser Pro Ala Ser
            420                 425                 430

Met Cys Ser Ala Thr Leu Thr Pro Ile Pro Ser Ala Ile Ser Leu Met
            435                 440                 445

Cys Cys Ala Thr Val Ile Thr Asp Gly Met Ser Lys Ala Ala Ile Trp
    450                 455                 460

Lys Arg Gln Arg Arg Tyr Trp Lys Lys Asn Phe Trp Pro Gly Arg Arg
465                 470                 475                 480

Asn Cys Ile Ser Arg Leu Ser Ser Pro Asn Thr Ala Trp Ile Arg Pro
                485                 490                 495

Gly Cys Thr Gln Cys Thr Pro Thr Cys Gly Val Lys Ser Ile Ser Val
            500                 505                 510

His Gly Trp Ile Cys Ile Thr Ala Ser Leu Ser Arg Gln Arg Arg Arg
            515                 520                 525

Arg Thr Gly Met Glu Phe Arg Arg Phe Cys Asp Leu Ala Arg His Ile
    530                 535                 540

Ala Arg Trp Arg Tyr Lys Lys Gly Ile Phe Thr Arg Asp Arg Lys Pro
545                 550                 555                 560

Lys Ser Ala Ala Phe Leu Leu Gln Lys Arg Trp Thr Gly Met Asn Phe
                565                 570                 575

Gly Glu Lys Pro Gln Gln Gly Gly Lys Gln
                580                 585

<210> SEQ ID NO 5
<211> LENGTH: 35
<212> TYPE: DNA
<213> ORGANISM: artificial sequence
<220> FEATURE:
<223> OTHER INFORMATION: a forward mutation primer sequence

<400> SEQUENCE: 5
cgcggatcca ttgccaccat ggatctttct ttcac                            35

<210> SEQ ID NO 6
<211> LENGTH: 28
<212> TYPE: DNA
<213> ORGANISM: artificial sequence
```

```
<220> FEATURE:
<223> OTHER INFORMATION: a reverse mutation primer sequence

<400> SEQUENCE: 6
ccggaattcg ttactcggtc tcagtgcc                                              28

<210> SEQ ID NO 7
<211> LENGTH: 29
<212> TYPE: DNA
<213> ORGANISM: artificial sequence
<220> FEATURE:
<223> OTHER INFORMATION: a forward primer sequence

<400> SEQUENCE: 7
cgcggatcca tggtccgtcc tgtagaaac                                             29

<210> SEQ ID NO 8
<211> LENGTH: 29
<212> TYPE: DNA
<213> ORGANISM: artificial sequence
<220> FEATURE:
<223> OTHER INFORMATION: a reverse primer sequence

<400> SEQUENCE: 8
ccggaattct cattgtttgc ctccctgct                                             29
```

PSEUDOTYPED INSECT BACULOVIRUS GENE TRANSFER SYSTEM AND PSEUDOTYPED BACULOVIRUS FOR SHRIMPS, CONSTRUCTION METHOD AND USE THEREOF

RELATED APPLICATIONS

This application is based on, and claims benefit of and priority to, Chinese Patent Application No. CN202010196617.0 filed on Mar. 19, 2020, the contents of which are hereby incorporated by reference in their entirety for all purposes.

SEQUENCE LISTING

The present application contains a Sequence Listing which has been submitted in ASCII format via EFS-Web and is hereby incorporated by reference in its entirety. Said ASCII copy, created on Mar. 19, 2020, is named SEQUENCE_LISTING_GWP202004365.txt and is 12 kB in size.

TECHNICAL FIELD

The present invention relates to the technical field of genetic engineering, and in particular, to a pseudotyped insect baculovirus gene transfer system and a pseudotyped baculovirus for shrimps, and a construction method and use thereof. That is, the present invention relates to a pseudotyped insect baculovirus gene transfer system exhibiting tropism for shrimps and a pseudotyped insect baculovirus exhibiting tropism for shrimps, and a construction method thereof, and use thereof in adult shrimp tissues and in vitro cultured shrimp cells.

BACKGROUND

Bac-to-Bac insect baculovirus expression system (Invitrogen) is a well-developed gene transfer technology for insect cells. The system consists of a transfer plasmid, a helper plasmid, a baculovirus plasmid (Bacmid) and a competent bacterial cell (DH10Bac). Based on the transposition of $E.\ coli$ transposase Tn7, the purpose to quickly recombine a foreign gene into the Bacmid in $E.\ coli$ and amplify the recombinant baculovirus is successfully achieved by this system. The transfer plasmid (pFASTBac1) is characterized in that the strong insect promoter $P_{PH}$ (promoter of polyhedrin gene) and the multiple cloning site thereafter are flanked by the left and right Tn7 transposase recognition sites, Tn7L and Tn7R, respectively. The baculovirus plasmid (Bacmid) is characterized in that a prokaryotic low-copy plasmid replicon (mini-F), a kanamycin resistance gene, and a LacZ gene with the transposase recognition site attTn7 inserted therein (non-frameshift insertion) are inserted. The helper plasmid is a transposase expression plasmid. The host cell of DH10Bac is an $E.\ coli$ competent cell stably transformed with the helper plasmid and the baculovirus plasmid.

The technical process of the insect baculovirus expression system is as follows: a foreign gene such as GUS (β-D-glucuronidase) is cloned to the multiple cloning site (MCS) of the transfer plasmid pFastBac1, and the recombinant plasmid pFastBac-GUS is purified; then the recombinant plasmid obtained is transformed into a $E.\ coli$ competent cell of DH10Bac, and under the action of transposase expressed by the helper plasmid, the GUS gene along with its promoter $P_{PH}$ is transposed to the attTn7 site in Bacmid; Bacmid-GUS recombinant plasmid is extracted and purified; Bacmid-GUS recombinant plasmid is transfected into an insect packaging cell of sf9, and a Bacmid-GUS recombinant virus is packaged and purified; and the packaged virus is used to infect a target cell to achieve the transfer and expression of the foreign gene in the target cell.

However, studies have shown that the insect baculovirus expression system cannot effectively infect a shrimp cell, indicating that the system has an extremely low tropism for a shrimp cell, and cannot be used for studies on the gene transfer in shrimp tissues and cells.

At present, owing to a lack of an efficient gene transfer and expression technology for adult shrimps and in vitro cultured shrimp cells, the development of researches on genetically modified shrimps and shrimp gene editing is significantly hampered.

SUMMARY

The present invention is intended to provide a pseudotyped insect baculovirus gene transfer system and a pseudotyped baculovirus for shrimps, and a construction method and use thereof. The pseudotyped insect baculovirus gene transfer system for shrimps disclosed in the present invention can achieve stable and efficient transfer and expression of a foreign gene in shrimp tissues and in vitro cultured shrimp cells.

The present invention provides a pseudotyped insect baculovirus gene transfer system for shrimps, including a Bac-to-Bac insect baculovirus expression system, an expression plasmid carrying a shrimp virus-source envelope protein gene and an insect packaging cell.

Preferably, the expression plasmid carrying shrimp virus-source envelope protein gene includes the expression plasmid carrying shrimp white spot syndrome virus (WSSV) envelope protein gene.

Preferably, the envelope protein gene in the shrimp virus envelope protein gene expression plasmid has a nucleotide sequence as shown in SEQ ID NO. 1.

Preferably, a framework vector for constructing the shrimp virus envelope protein gene expression plasmid includes pcDNA3.1.

The present invention also provides a construction method of a pseudotyped insect baculovirus for shrimps based on the gene transfer system according to the above technical solution, including the following steps:
1) constructing, with a Bac-to-Bac insect baculovirus expression system, an insect baculovirus recombinant plasmid carrying a foreign gene; and
2) co-transfecting the insect baculovirus recombinant plasmid obtained in step 1) and the expression plasmid carrying the shrimp virus envelope protein gene into an insect packaging cell to obtain a pseudotyped insect baculovirus for shrimps.

The present invention also provides a pseudotyped insect baculovirus for shrimps constructed by the construction method based on the above technical solution.

The present invention also provides the use of the gene transfer system based on the above technical solution or the pseudotyped insect baculovirus for shrimps based on the above technical solution in the expression of a foreign gene in a shrimp cell.

Preferably, the shrimp cell includes an in-vitro-cultivated shrimp cell, and the in-vitro-cultivated shrimp cell includes a primarily cultured shrimp peripheral hemolymph cells.

The present invention also provides the use of the gene transfer system based on the above technical solution or the pseudotyped insect baculovirus for shrimps based on the above technical solution in the expression of a foreign gene in an adult shrimp tissue.

Preferably, the adult shrimp tissue includes gill, heart and intestine tissues of an adult shrimp.

The invention provides a pseudotyped insect baculovirus gene transfer system for shrimps. The gene transfer system disclosed in the present invention is a system obtained from an improvement based on the existing Bac-to-Bac insect baculovirus expression system. A shrimp virus envelope protein is introduced into a baculovirus envelope by co-transfecting an expression plasmid carrying shrimp virus envelope protein gene and an insect baculovirus recombinant plasmid carrying a foreign gene, obtained by a Bac-to-Bac insect baculovirus expression system, into an insect packaging cell. With significantly-improved packaging efficiency and tropism for a shrimp cell, the obtained pseudotyped baculovirus can be successfully used for studies on gene transfer in adult shrimps and shrimp cells, and the shortcomings of the prior art are overcome.

The system of the present invention has the following advantages: (1) Compared with the existing Bac-to-Bac insect baculovirus expression system on the market that cannot infect shrimps (such as, adult shrimp tissues and in-vitro-cultivated shrimp cells), the system of the present invention has a significantly-higher infection and expression ability in adult shrimp tissues, exhibiting 100% infection and expression instead. (2) The envelope protein gene in the system of the present invention exists independently of the baculovirus plasmid (Bacmid), and only intends to increase the packaging efficiency for baculovirus and the infection and expression efficiency, and the plasmid DNA thereof will not enter a shrimp cell, thereby improving the biological safety of the system. (3) In the system of the present invention, the problem that the gene transfer is difficult to achieve for adult shrimps and shrimp cells (in-vitro-cultivated shrimp cells), and any foreign gene can be efficiently transferred to and expressed in a shrimp cell.

DETAILED DESCRIPTION

Figure 1:
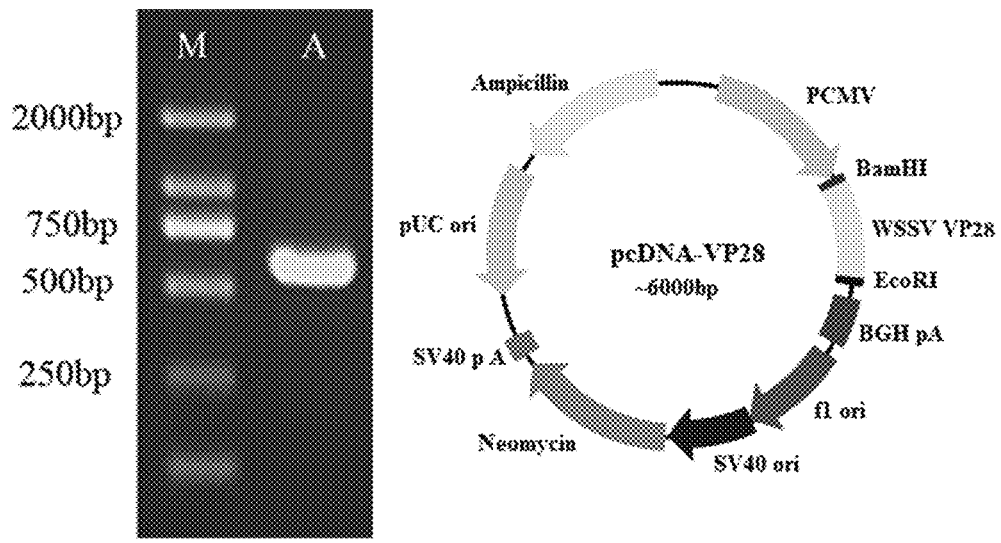
FIG. 1 is the electrophoresis result for the amplification of the open reading frame of VP28 gene cloned in the present invention and the map for pcDNA-VP28 plasmid.
Figure 2:
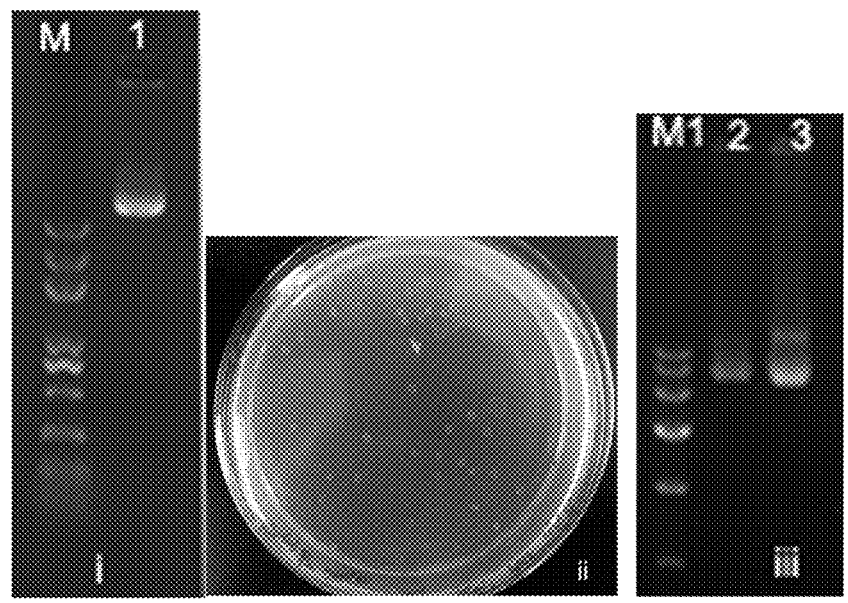
FIG. 2 is a diagram of the preparation of the recombinant baculovirus plasmid of Bacmid-GUS provided by the present invention.
Figure 3:
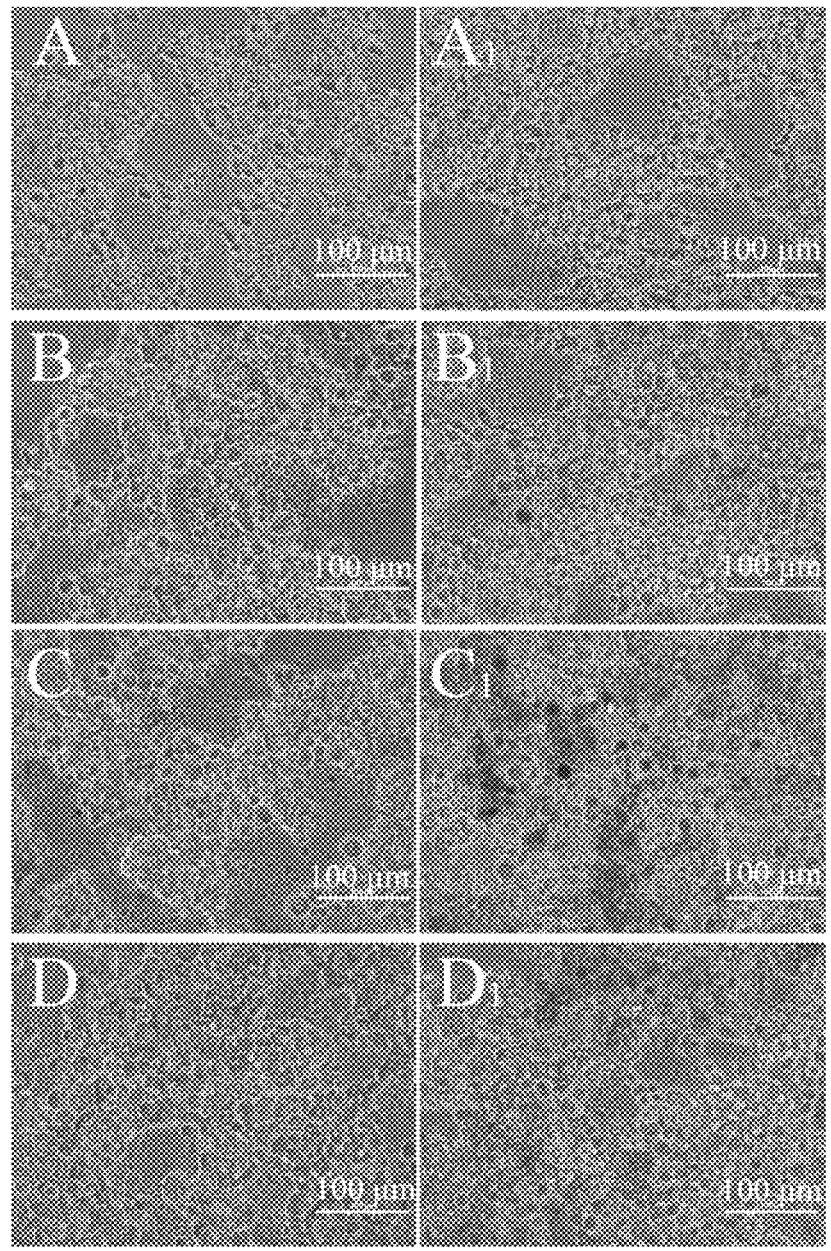
FIG. 3 shows the optimization of the optimal conditions for the transfection of the Bacmid-GUS plasmid provided by the present invention in sf9 cells.

The present invention provides a pseudotyped insect baculovirus gene transfer system for shrimps, including a Bac-to-Bac insect baculovirus expression system, a shrimp virus envelope protein gene expression plasmid and an insect packaging cell. Specifically, the pseudotyped insect baculovirus gene transfer system for shrimps disclosed in the present invention is obtained from the successful modification based on an insect baculovirus expression system by preparing a pseudotyped insect baculovirus. In this system, the tropism for adult shrimp tissues and in-vitro-cultivated shrimp cells and the infection and expression efficiency are significantly improved. In a specific embodiment of the present invention, a virus, with an envelope that includes both the envelope protein derived from an insect baculovirus and the envelope protein VP28 derived from a shrimp virus, is prepared. In the present invention, the Bac-to-Bac insect baculovirus expression system includes a transfer plasmid (pFASTBac1), a helper plasmid, a baculovirus plasmid (Bacmid), and a competent cell (DH10Bac). The baculovirus plasmid (Bacmid) carries a prokaryotic low-copy plasmid replicon (mini-F), a kanamycin resistance gene, and a LacZ gene with the transposase recognition site attTn7 inserted therein (non-frameshift insertion). A foreign gene can be recombined to the transposase recognition site of attTn7 to form an insect baculovirus recombinant plasmid carrying the foreign gene.

In the present invention, the expression plasmid carrying shrimp virus envelope protein gene includes the expression plasmid carrying WSSV envelope protein gene. In the present invention, the WSSV envelope protein preferably includes VP28, VP19 and the like. In a specific embodiment of the present invention, the WSSV envelope protein is preferably VP28, and more preferably modified VP28 driven by a cytomegalovirus (CMV) promoter (hereafter, VP28 mentioned in the present invention refers to modified shrimp virus envelope protein VP28). In the present invention, the envelope protein gene in the shrimp virus envelope protein gene expression plasmid has a nucleotide sequence as shown in SEQ ID NO. 1. The corresponding amino acid sequence is shown as SEQ ID NO. 2. The plasmid including the nucleotide sequence shown as SEQ ID NO. 1 of the present invention can efficiently express the VP28 protein of a shrimp virus in insect cells sf9. In the present invention, a framework vector for constructing the shrimp virus envelope protein gene expression plasmid includes pcDNA3.1. When the envelope protein is VP28, the corresponding plasmid is an eukaryotic expression vector pcDNA-VP28. In the present invention, by co-transfecting the pcDNA-VP28 plasmid with an insect baculovirus (Bacmid) recombinant plasmid into packaging cells, the packaging efficiency for an insect baculovirus can be significantly improved, and the introduction of the shrimp virus envelope protein into the envelope of the packaged virus greatly increases the tropism for a shrimp cell.

The present invention also provides a construction method of a pseudotyped insect baculovirus for shrimps based on the gene transfer system according to the above technical solution, including the following steps:

1) constructing, with a Bac-to-Bac insect baculovirus expression system, an insect baculovirus recombinant plasmid carrying a foreign gene; and
2) co-transfecting the insect baculovirus recombinant plasmid obtained in step 1) and the expression plasmid carrying shrimp virus envelope protein gene into an insect packaging cell to obtain a pseudotyped insect baculovirus for shrimps.

In the present invention, an insect baculovirus recombinant plasmid carrying a foreign gene is constructed using a Bac-to-Bac insect baculovirus expression system. In the present invention, no special restriction is imposed on the construction method, and a Bac-to-Bac insect baculovirus expression system well known to those skilled in the art may be adopted.

In the present invention, after an insect baculovirus recombinant plasmid is obtained, the insect baculovirus recombinant plasmid is co-transfected with the expression plasmid carrying shrimp virus envelope protein gene into an insect packaging cell to obtain a pseudotyped insect baculovirus for shrimps. Conditions for the co-transfection are not particularly defined in the present invention. In a specific embodiment, the Bacmid-GUS recombinant virus plasmid and pcDNA3.1-VP28 of the present invention are co-transfected at a ratio preferably of 3:1. After co-transfection, preferably, the steps of collecting the cell culture supernatant, purifying and concentrating are also included in the present invention. The pseudotyped insect baculovirus for shrimps constructed by the construction method of the present invention can efficiently infect adult shrimps and shrimp cells.

Specifically, in the present invention, an insect baculovirus recombinant plasmid carrying a foreign gene is co-transfected with the expression plasmid pcDNA-VP28 into an insect cell sf9; 4 days later, the cell culture supernatant is collected and centrifuged to obtain a first passage (P1) virus supernatant; the first passage virus is used to infect a cell sf9; 4 days later, the cell culture supernatant is collected again and centrifuged to obtain a second passage (P2) virus supernatant; and the second passage virus supernatant is ultra-centrifuged, purified and concentrated to obtain a pseudotyped insect baculovirus exhibiting tropism for a shrimp cell. The envelope of a virion obtained in the present invention includes not only the envelope protein derived from an insect baculovirus, but also the envelope protein VP28 derived from a shrimp virus. The introduction of the shrimp virus envelope protein VP28 in the present invention can greatly improve the packaging efficiency and the tropism for a shrimp cell of the pseudotyped insect baculovirus. In a more specific embodiment of the present invention, the pseudotyped baculovirus Bacmid-GUS/VP28 is prepared preferably as follows: with the transfection reagent Cellfectin II (Invitrogen), the Bacmid-GUS recombinant virus plasmid and the pcDNA-VP28 plasmid are co-transfected into an insect cell sf9 at a ratio of 3:1, and a virus is packaged; 4 days later, a cell culture supernatant is collected and centrifuged to obtain a P1 virus; the P1 virus is used to infect a cell sf9 for amplification; 4 days later, the cell culture supernatant is collected and filtered by a 0.45 μm filter membrane; the filtrate is ultra-centrifuged to isolate and purify the P2 virus; and the obtained virus is dispensed and stored in a refrigerator at −80° C.

The present invention also provides a pseudotyped insect baculovirus for shrimps constructed by the construction method based on the above technical solution. The infection and expression of the virus of the present invention in adult shrimp tissues are tissue-specific, and the infection and expression efficiency in gill, heart and intestine tissues of a shrimp can be as high as 100%, but no expression of a foreign gene can be detected in Oka organs and muscle tissues. The infection and expression of the virus of the present invention in shrimp cells (in-vitro-cultivated cells) are also cell-specific, and the virus can successfully infect an in-vitro-cultivated shrimp peripheral hemolymph cells, but cannot infect an in-vitro-cultivated shrimp embryonic cell.

The present invention also provides the use of the gene transfer system based on the above technical solution or the pseudotyped insect baculovirus for shrimps based on the above technical solution in the expression of a foreign gene in a shrimp cell.

In the present invention, the shrimp cell includes an in-vitro-cultivated shrimp cell, and the in-vitro-cultivated shrimp cell includes a primary shrimp peripheral hemolymph cells.

In the present invention, the adult shrimp tissue includes gill, heart and intestine tissues of an adult shrimp.

In a specific embodiment of the present invention, with GUS reporter gene (β-D-glucuronidase) as a foreign gene, a Bac-to-Bac insect baculovirus expression system (Cat. No. 10359-016) of Invitrogen is improved as follows: GUS reporter gene is cloned to the multiple cloning site of a transfer plasmid of pFastBac1, and the recombinant plasmid pFastBac-GUS is purified; the recombinant plasmid pFastBac-GUS is transformed into an *E. coli* competent cell DH10Bac, and GUS is transposed to the attTn7 site in Bacmid to obtain a recombinant virus plasmid Bacmid-GUS; the recombinant virus plasmid Bacmid-GUS is extracted and purified; the obtained Bacmid-GUS recombinant virus plasmid DNA and the pcDNA-VP28 plasmid are co-transfected into a packaging cell sf9, and a pseudotyped baculovirus Bacmid-GUS/VP28 is obtained by packaging; the pseudotyped baculovirus Bacmid-GUS/VP28 is purified and concentrated, and the virus titer is determined; and the packaged virus is used to infect an adult shrimp tissue or in-vitro-cultivated shrimp cell to achieve the transfer and expression of the foreign gene in the target tissue or cell. In the present invention, the nucleotide sequence of the GUS reporter gene is shown as SEQ ID NO. 3, and the amino acid sequence of a protein corresponding to the GUS reporter gene is shown as SEQ ID NO. 4.

The transfer plasmid pFastBac1, *E. coli* competent cell DH10Bac and packaging cell sf9 involved in the present invention are all derived from the Bac-to-Bac insect baculovirus expression system (Cat. No. 10359-016).

The transfer plasmid pFASTBac1 includes a strong insect promoter $P_{PH}$ (polyhedrin gene promoter), a multiple cloning site, and the flanking Tn7 transposase recognition sites of Tn7R and Tn7L.

The host cell DH10Bac is an *E. coli* competent cell stably transformed with a helper plasmid and a baculovirus plasmid (Bacmid).

The baculovirus plasmid (Bacmid) includes a prokaryotic low-copy plasmid replicon (mini-F), a kanamycin resistance gene (Kan$^r$), and a LacZ gene with the transposase recognition site attTn7 inserted therein (non-frameshift insertion). The helper plasmid is a transposase expression plasmid.

In the present invention, the titer of the packaged virus is determined as follows: a concentrated virus solution is used to infect sf9 cells; X-Gluc (Solarbio Science & Technology Co., Ltd.) staining is performed, and Sf9 cells stained into blue is counted; and titer is calculated for the concentrated virus solution.

In the present invention, an adult shrimp tissue is infected with the virus as follows: a concentrated virus solution is injected into an adult shrimp muscle tissue; and 4 days later, different shrimp tissues are taken for X-Gluc staining to observe the expression of the GUS reporter gene.

In the present invention, an in-vitro-cultivated shrimp cell is infected with the virus as follows: the original medium for the in-vitro-cultivated shrimp cell is replaced with an antibiotic- and serum-free medium; a concentrated virus solution is added to the culture supernatant at a certain amount; and 4 days later, X-Gluc staining is performed to observe the expression of the GUS reporter gene.

The pseudotyped insect baculovirus gene transfer system and virus for shrimps, and the construction method and use thereof disclosed in the invention are further described in detail below with reference to specific examples. The technical solutions of the present invention include, but are not limited to, the following examples.

Example 1

Cloning and modification of the open reading frame nucleic acid sequence of shrimp WSSV virus envelope protein gene (VP28), and construction of eukaryotic expression vector pcDNA3.1-VP28 for the gene.

Genomic DNA of a WSSV-infected shrimp was extracted using a DNA extraction kit of Transgen Biotech Co., LTD (Easypure Marine Animal Genomic DNA kit, Cat. No. EE151-01), and the specific operations were carried out according to the kit instructions. The nucleic acid sequence of the open reading frame of shrimp virus VP28 gene was improved by PCR amplification primers, that is, VP28 gene-specific primers along with BamHI and EcoRI restriction sites were designed: a forward mutation primer sequence: 5'-CGCGGATCCATTGCCACCATGGATCTTTCTTTCAC-3' (SEQ ID NO. 5); and a reverse mutation primer sequence: 5'-CCGGAATTCGTTACTCGGTCTCAGTGCC-3' (SEQ ID NO. 6). The target fragment was obtained by PCR amplification. The PCR reaction system and procedure were as follows: the 50 μl reaction system consisted of 5.0 μl 10×PCR buffer (including $Mg^{2+}$), 4.0 μl 2.5 mmol/L dNTPs, 2.5 μL 10 μmol/L upstream and downstream primers, 0.5 μL 5 IU/μL Taq DNA polymerase, 2 μL genomic DNA, and 33.5 μL $ddH_2O$; and the PCR reaction procedure included: pre-denaturation at 95° C. for 10 min; 30 repetitions of the following cycle: denaturation at 95° C. for 45 s, annealing at 60° C. for 45 s, and extension at 72° C. for 50 s; and final extension at 72° C. for 10 min. The PCR product was assayed by 1% agarose gel electrophoresis, and sent to a sequencing company for sequencing. (FIG. 1, the left panel, where M is 2,000 DNA Molecular Weight Marker, and A is the amplification product for VP28).

A plasmid pcDNA3.1-V5/HisA (Invitrogen) was digested with BamHI and EcoRI endonucleases, and a VP28 sequence (SEQ ID NO: 1) carrying the same cohesive termini (BamHI/EcoRI) was inserted therein to obtain pcDNA-VP28 (FIG. 1, the right panel). FIG. 1 is the electrophoresis result for VP28 open reading frame cloned in the present invention and the map for pcDNA-VP28 plasmid.

Example 2

The cloning of a foreign gene into a donor plasmid pFastBac1.

The construction of pFastBac1-GUS recombinant plasmid was adopted as an example (FIG. 2, a diagram for preparing the recombinant baculovirus plasmid Bacmid-GUS, where, i is the electrophoresis result for pFastBac1-GUS plasmid DNA, ii is the blue-white screening result for the recombinant baculovirus plasmid Bacmid-GUS, and iii is the extraction and electrophoresis results for the recombinant baculovirus plasmid Bacmid-GUS).

GUS gene-specific primers including BamHI and EcoRI restriction sites were designed: a forward primer sequence: 5'-CGCGGATCCATGGTCCGTCCTGTAGAAAC-3' (SEQ ID NO. 7); and a reverse primer sequence: 5'-CCGGAATTCTCATTGTTTGCCTCCCTGCT-3' (SEQ ID NO. 8). The target fragment was obtained by PCR amplification. The PCR reaction system and procedure were as follows: the 50 μL reaction system consisted of 25 μL 2× Hieff PCR Master Mix (including $Mg^{2+}$), 2.5 μL 10 μmol/L upstream and downstream primers, 2 μL genomic DNA, and 18 L $ddH_2O$; and the PCR reaction procedure included: pre-denaturation at 95° C. for 5 min; 30 repetitions of the following cycle: denaturation at 95° C. for 45 s, annealing at 55° C. for 45 s, and extension at 72° C. for 90 s; and final extension at 72° C. for 10 min. The PCR product was assayed by 1% agarose gel electrophoresis, and sent to a sequencing company for sequencing.

A plasmid pFastBac1 (Invitrogen) was digested with BamHI and EcoRI endonucleases, and a GUS sequence carrying the same cohesive termini (BamHI/EcoRI) was inserted therein to obtain pFastBac1-GUS.

Example 3

Recombination of a foreign gene into a virus plasmid Bacmid.

The construction of Bacmid-GUS was adopted as an example (FIG. 2).

A pFastBac1-GUS plasmid was transformed into DH10Bac competent cells. The transformed product was plated, and blue-white screening and bacterial PCR detection were performed to obtain a recombinant Bacmid including GUS gene: Bacmid-GUS.

Example 4

Preparation, concentration and purification of a recombinant baculovirus.

Bacmid-GUS was adopted as an example.

Bacmid-GUS recombinant baculovirus plasmid DNA was transfected into Sf9 insect cells using Cellfectin II transfection reagent. The optimization result of the optimal conditions for transfection of Bacmid-GUS plasmid in sf9 cells is shown in FIG. 3, where, A and A1 are images of control cells before and after GUS staining, B and B1, C and C1, and D and D1 are respectively images of Sf9 cells transfected with Bacmid-GUS plasmid and Cellfectin II transfection reagent at a ratio of 1:4, 1:5 and 1:6 (μg:μL) before and after GUS staining, the results show that the optimal transfection can be achieved when the plasmid DNA and the transfection reagent are used at a ratio of 1:5 (μg μ:L). P1 virus was collected to infect sf9 cells once again, the insect baculovirus was amplified, and then P2 virus was isolated and purified (A to D in FIG. 5).

X-gluc staining was performed to detect the protein expression of the GUS gene. The specific method was as follows: the medium in a culture well was discarded; the monolayer cells were washed with PBS, and added with a cell fixative including 2% formaldehyde and 0.05% glutaraldehyde for 5 min of fixation at room temperature; the fixative was discarded, and the cells were washed twice with PBS and added with 20 mg/mL X-Gluc for staining; the cells were incubated at 28° C. for 12 h; and the staining results were recorded by a light microscope.

Example 5

Preparation, concentration and purification of a pseudotyped insect baculovirus.

Bacmid-GUS/VP28 was adopted as an example.

Figure 4:
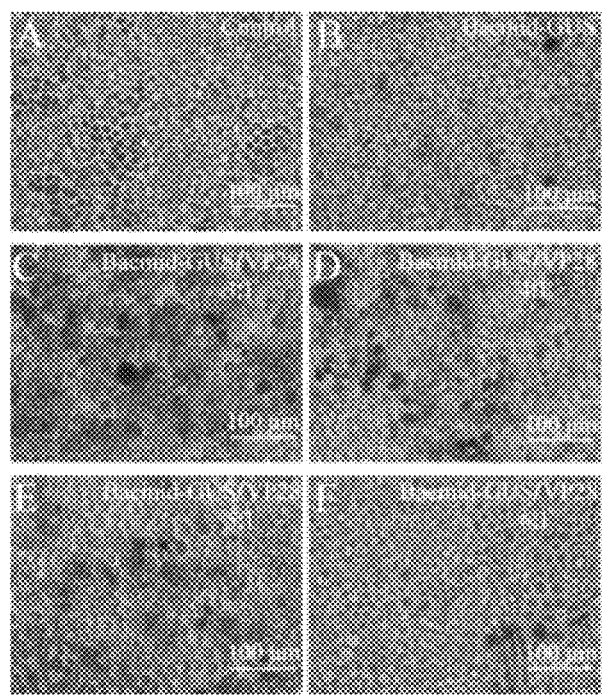
FIG. 4 shows the research results of the optimal packaging conditions for the pseudotyped baculovirus of Bacmid-GUSNP28 provided by the present invention in packaging cells Sf9, and the packaging efficiency comparison between Bacmid-GUSNP28 and Bacmid-GUS.

A pseudotyped baculovirus Bacmid-GUS/VP28 was obtained from successful packaging by co-transfecting the plasmid Bacmid-GUS and pcDNA-VP28 into insect cells Sf9. As shown in FIG. 4 (research results of the optimal packaging conditions for pseudotyped baculovirus Bacmid-GUS/VP28 in Sf9 packaging cells, and comparison of packaging efficiency between Bacmid-GUS/VP28 and Bacmid-GUS, where, A is untransfected control cells, B is the packaging result from the transfection of Bacmid-GUS plasmid, and C, D, E and F are the packaging results from the co-transfection of plasmid Bacmid-GUS and pcDNA-VP28 into sf9 cells at a ratio of 3:1, 4:1, 5:1 and 6:1; and for all cells, DNA and transfection reagent are used at ratio of 1:5 (μg:μL)), the optimal ratio of Bacmid-GUS and pcDNA-VP28 for co-transfection is 3:1, and the introduction of plasmid pcDNA-VP28 greatly improves the packaging efficiency for virus Bacmid-GUS/VP28.

Figure 5:
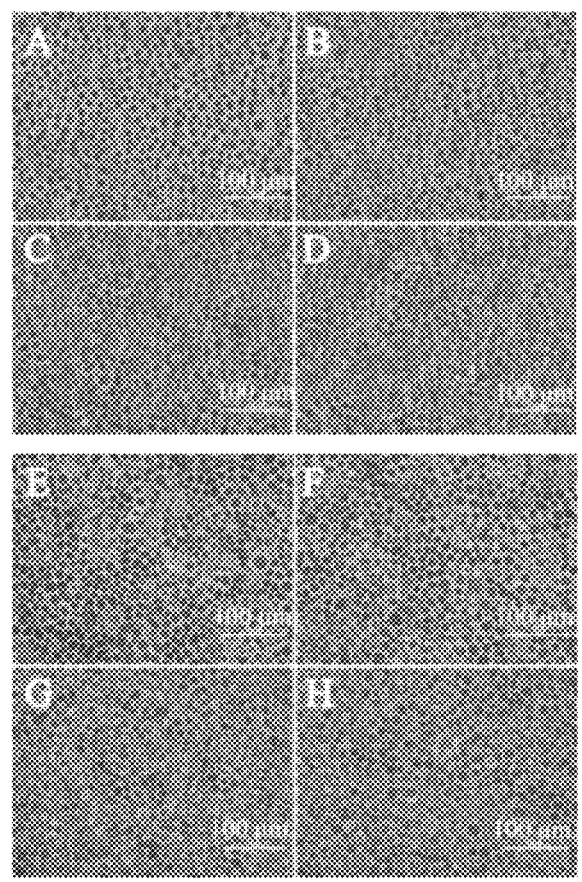
FIG. 5 shows the P2 amplification results for the two baculoviruses of Bacmid-GUS and Bacmid-GUS/VP28 provided by the present invention in Sf9 cells.

P1 virus was collected to infect sf9 cells once again, the insect baculovirus was amplified, and then P2 virus was isolated and purified (E to H in FIG. 5). FIG. 5 shows the P2 amplification results of two baculoviruses of Bacmid-GUS and Bacmid-GUS/VP28 in Sf9 cells, where, A, B, C and D are images of sf9 cells on days 1, 2, 3 and 4 after the infection of baculovirus Bacmid-GUS; E, F, G and H are images of sf9 cells on days 1, 2, 3 and 4 after the infection of pseudotyped baculovirus Bacmid-GUS/VP28, and 400 μl of P1 virus supernatant is inoculated to each 10-cm culture dish for transfection.

Example 6

Titer determination for an insect baculovirus.

The virus titer was determined by the expression of the GUS reporter gene. The infection of baculovirus Bacmid-GUS or Bacmid-GUS/VP28 in Sf9 cells was taken as an example. The baculovirus Bacmid-GUS or Bacmid-GUS/VP28 solution was serially diluted to $10^{-1}$-$10^{-7}$ times with serum- and penicillin/streptomycin-free SIM insect cell culture medium, and then 100 μL of the virus dilution was added to each well of the 96-well cell culture plate; and on day 4 after the infection, X-gluc staining was performed to detect the expression of the GUS reporter gene, and the virus titer was calculated. Calculation formula: virus titer TU/mL (transduction units per mL)=positive cells %×total cells× dilution factor/virus solution volume (mL).

Figure 6:
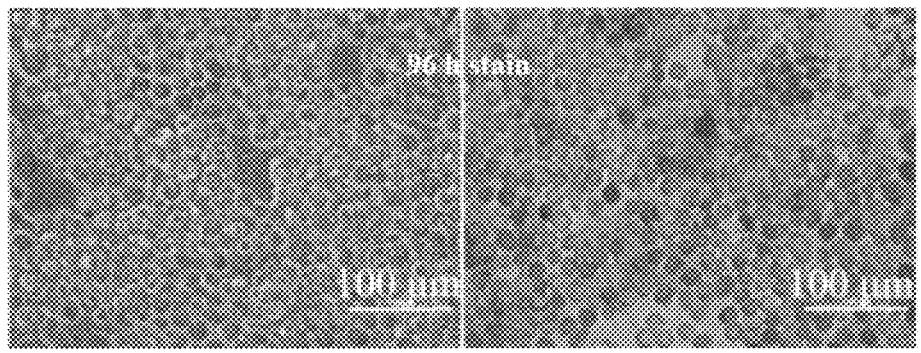
FIG. 6 shows the GUS staining result obtained 96 h after the infection of the baculovirus Bacmid-GUS provided by the present invention in Sf9 cells.

As shown in FIG. 6 (GUS staining results of Sf9 cells obtained 96 h after the infection of baculovirus Bacmid-GUS, where, the left and right panels are images of Sf9 cells infected with recombinant baculovirus Bacmid-GUS before and after GUS staining respectively, with a virus titer of $5.3 \times 10^8$ TU/ml), the virus titer of Bacmid-GUS can reach $5.3 \times 10^8$ TU/mL.

Figure 7:
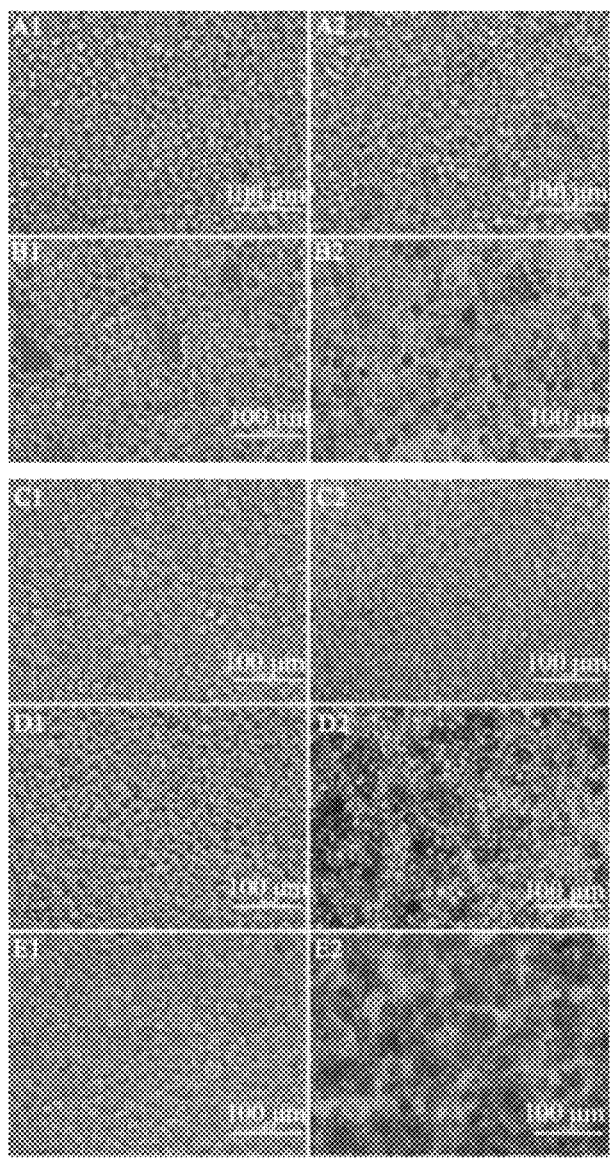
FIG. 7 shows the test results obtained 96 h after the infection of pseudotyped baculovirus Bacmid-GUS/VP28 provided by the present invention in Sf9 cells.

As shown in FIG. 7 (the test results obtained 96 h after the infection of pseudotyped baculovirus Bacmid-GUS/VP28 in Sf9 cells,
where, A1 and A2 are images of control cells before and after GUS staining respectively; B1 and B2 are the virus titer determination results of concentrated P2 Bacmid-GUS virus solutions, and the virus titer can reach $5.3 \times 10^8$ TU/ml; C1 and C2 are images of control cells before and after GUS staining, respectively; D1 and D2 are the virus titer determination results of P1 Bacmid-GUS/VP28 pseudotyped baculovirus supernatant, and the virus titer can reach $5 \times 10^7$ TU/ml; and E1 and E2 are the virus titer determination results of concentrated P2 Bacmid-GUS/VP28 pseudotyped baculovirus solutions, and the virus titer of Bacmid-GUS/VP28 can reach $3 \times 10^{10}$ TU/mL.

Example 7

Infection of an Insect Baculovirus in an In-Vitro-Cultivated Shrimp Cell

The infection of Baculovirus of Bamcid-GUS and Bacmid-GUS/VP28 in primarily cultured shrimp peripheral hemolymph cells and embryonic cells was adopted as an example.

Figure 8:
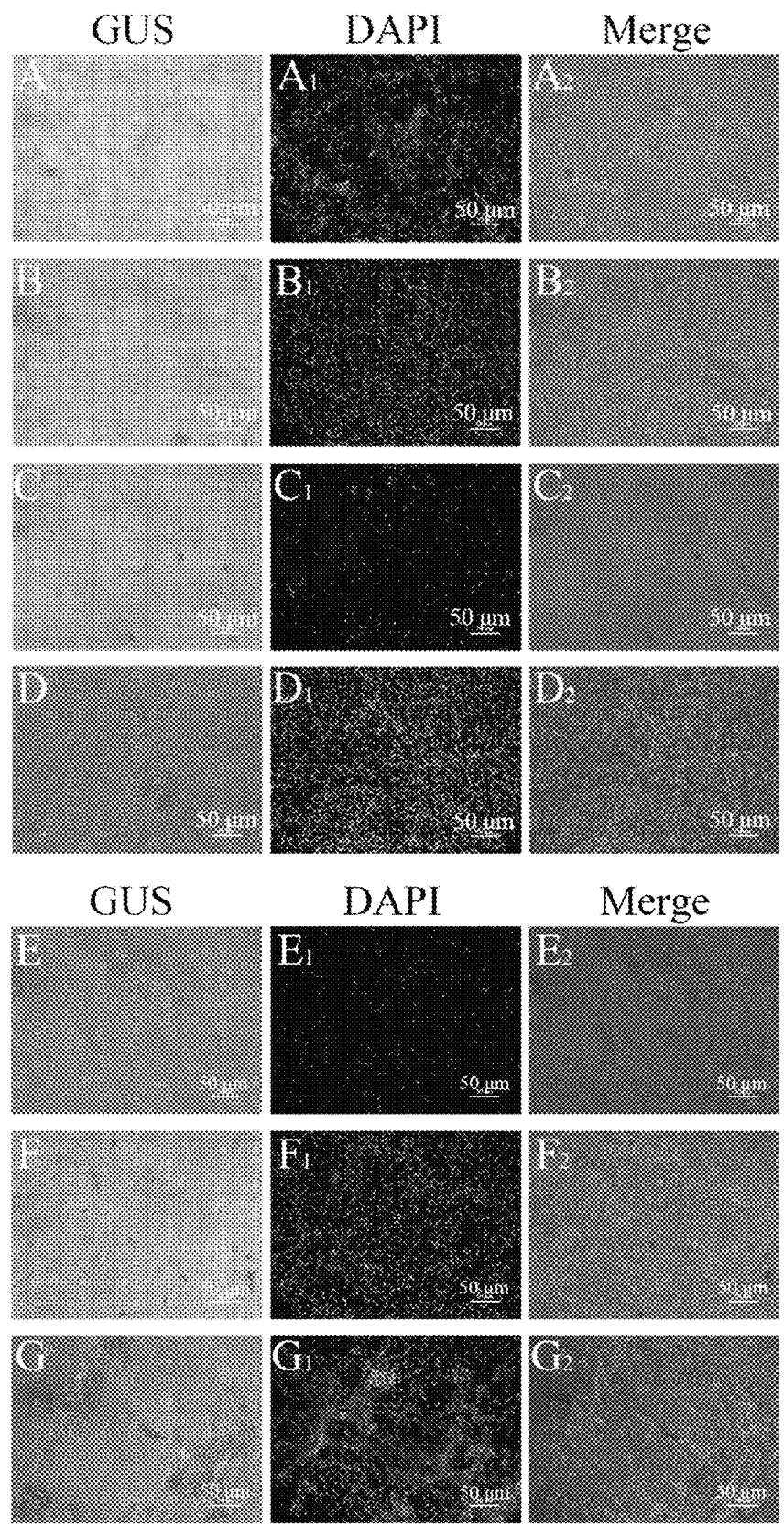
FIG. 8 shows that the pseudotyped baculovirus Bacmid-GUSNP28 can infect primarily cultured shrimp peripheral hemolymph cells, and the protein expression of GUS gene can be detected, while Bacmid-GUS virus cannot successfully infect primarily cultured shrimp peripheral hemolymph cells.

The primarily cultured shrimp peripheral hemolymph cells were infected with the virus as follows: the primarily cultured shrimp peripheral hemolymph cells were inoculated to a 48-well cell culture plate; after hemolymph cells grew adherently for 5 h, the original medium was discarded, and 100 μL of concentrated virus solution (diluted with 1.5×L-15 medium) was added to each well; after the virus was incubated for 4 h, the medium was replaced with the normal 1.5×L-15 complete medium; and on day 5 after virus infection, X-Gluc staining was performed to detect the expression of the GUS reporter gene. As shown in FIG. 8 (where, pseudotyped baculovirus Bacmid-GUS/VP28 can infect the primarily cultured shrimp peripheral hemolymph cells, and the protein expression of GUS gene can be detected, while Bacmid-GUS virus cannot successfully infect the primarily cultured shrimp peripheral hemolymph cells; A to G in the left column are the GUS staining results, A1 to G1 in the middle column are the nuclear DAPI fluorescence staining results, and A2 to G2 in the right column are the merged images of the first two images in the same row; the GUS expression is detected 120 h after virus infection; A, A1 and A2: control cells without virus supernatant treatment; B, B1 and B2: results of Bacmid-GUS virus infection at $3.0 \times 10^7$ TU/well; C, C1 and C2: results of Bacmid-GUS virus infection at $1.5 \times 10^8$ TU/well; D, D1 and D2: results of Bacmid-GUS virus infection at $3.0 \times 10^8$ TU/well; E, E1 and E2: results of Bacmid-GUS/VP28 pseudotyped virus infection at $3.0 \times 10^7$ TU/well; F, F1 and F2: results of Bacmid-GUSNP28 pseudotyped virus infection at $1.5 \times 10^8$ TU/well; G, G1 and G2: results of Bacmid-GUSNP28 pseudotyped virus infection at $3.0 \times 10^8$ TU/well; and scale bar=100 μm), baculovirus Bacmid-GUS cannot infect the primarily cultured shrimp peripheral hemolymph cells, and no significant GUS expression signal is observed after staining (B to D in FIG. 8). The results also show that there is no background expression of the GUS gene in a shrimp cell, thus GUS gene can be used for transgenic research on shrimps. Pseudotyped baculovirus Bacmid-GUSNP28 can efficiently infect the primarily cultured shrimp peripheral hemolymph cells, and significant GUS gene expression signal can be observed (G in FIG. 8) at a titer of $3 \times 10^8$ TU/mL.

Above results also show that an unmodified insect baculovirus Bac-to-Bac gene transfer and expression system exhibits an extremely low tropism for a shrimp cell, and cannot directly be used for studies on the gene transfer in shrimp cells. The introduction of VP28 envelope protein of the shrimp virus can significantly improve the tropism of the pseudotyped baculovirus Bacmid-GUSNP28 for shrimp peripheral hemolymph cells, thereby facilitating the infection and expression of the pseudotyped baculovirus in shrimp peripheral hemolymph cells.

Figure 9:
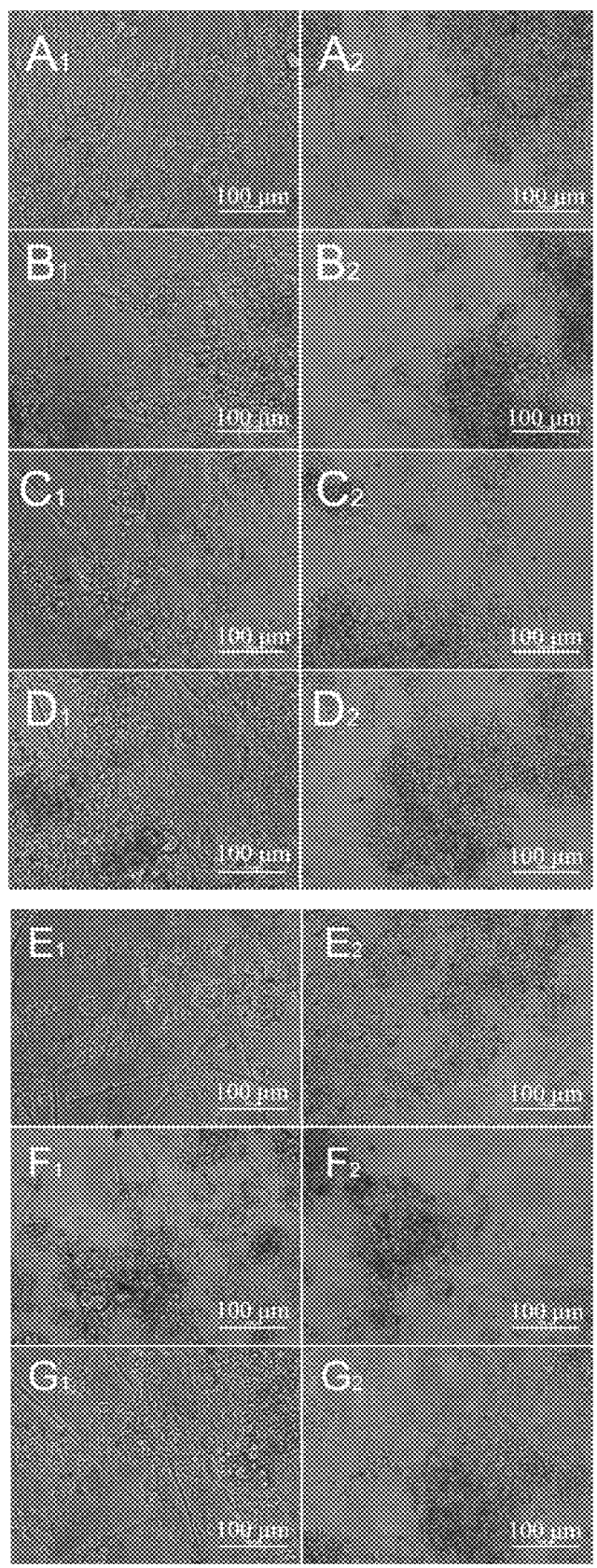
FIG. 9 shows that the two baculoviruses of Bacmid-GUSNP28 and Bacmid-GUS provided by the present invention both cannot infect primary shrimp embryonic cells, and the GUS expression cannot be detected.

The primary shrimp embryonic cells were infected with the virus as follows: shrimp embryonic cells were inoculated to a 48-well cell culture plate; after embryonic cells grew adherently for 2 days, the original medium was discarded, and 100 μL of concentrated virus solution (diluted with 1.5×L-15 medium) was added to each well; after the virus was incubated for 4 h, the medium was replaced with the normal 1.5×L-15 complete medium; and on day 5 after virus infection, X-Gluc staining was performed to detect the expression of the GUS reporter gene. As shown in FIG. 9 (baculoviruses Bacmid-GUS/VP28 and Bacmid-GUS both cannot infect primary shrimp embryonic cells, and GUS expression cannot be detected, where, A1 to G1 in the left column are images of cells before GUS staining, and A2 to G2 in the right column are images of cells after GUS staining, with the cells being the same at the same row; A1 and A2: control cells without virus supernatant treatment; the GUS expression is detected 120 h after virus infection; B1 and B2: results of Bacmid-GUS virus infection at $3.0 \times 10^7$ TU/well; C1 and C2: results of Bacmid-GUS virus infection at $1.5 \times 10^8$ TU/well; D1 and D2: results of Bacmid-GUS virus infection at $3.0 \times 10^8$ TU/well; E1 and E2: results of Bacmid-GUS/VP28 pseudotyped baculovirus infection at $3.0 \times 10^7$ TU/well; F1 and F2: results of Bacmid-GUS/VP28 pseudotyped baculovirus infection at $1.5 \times 10^8$ TU/well; G1 and G2: results of Bacmid-GUS/VP28 pseudotyped baculovirus infection at $3.0 \times 10^8$ TU/well; and scale bar=100 μm), the two baculoviruses Bacmid-GUS and Bacmid-GUS/VP28 both cannot efficiently infect primary shrimp embryonic cells, and the GUS gene expression cannot be detected. It indicates that the infection of pseudotyped baculovirus constructed by the present invention in shrimp cells is cell-specific, which may be related to the shrimp virus envelope protein VP28 used by the present invention.

X-Gluc staining is performed on shrimp cells in the same manner as that for Sf9 insect cells.

Example 8

Infection of an Insect Baculovirus in an Adult Shrimp Tissue

Bacmid-GUS and Bacmid-GUS/VP28 were adopted as examples.

The infection of above two baculoviruses in adult shrimps was conducted by intramuscular injection. The specific method was as follows: with a microsyringe, a baculovirus was injected at a site about 1 mm to the right of the middle abdominal line between the first pair of natatorial legs of a shrimp; after injection, the injection site was gently pressed, and then the shrimp was placed in sea water; on day 5 after virus injection, gill, Oka organ, heart, muscle and intestine tissues were taken from the shrimp and placed in 1.5 mL centrifuge tubes separately; tissue-specific GUS staining solution was added to each tube, and the resulting mixture was incubated in a 28° C. incubator for 12 h in the dark; then each tissue was washed with PBS to remove the staining solution; and images were acquired for each tissue by a stereomicroscope and the staining results were recorded.

Figure 10:
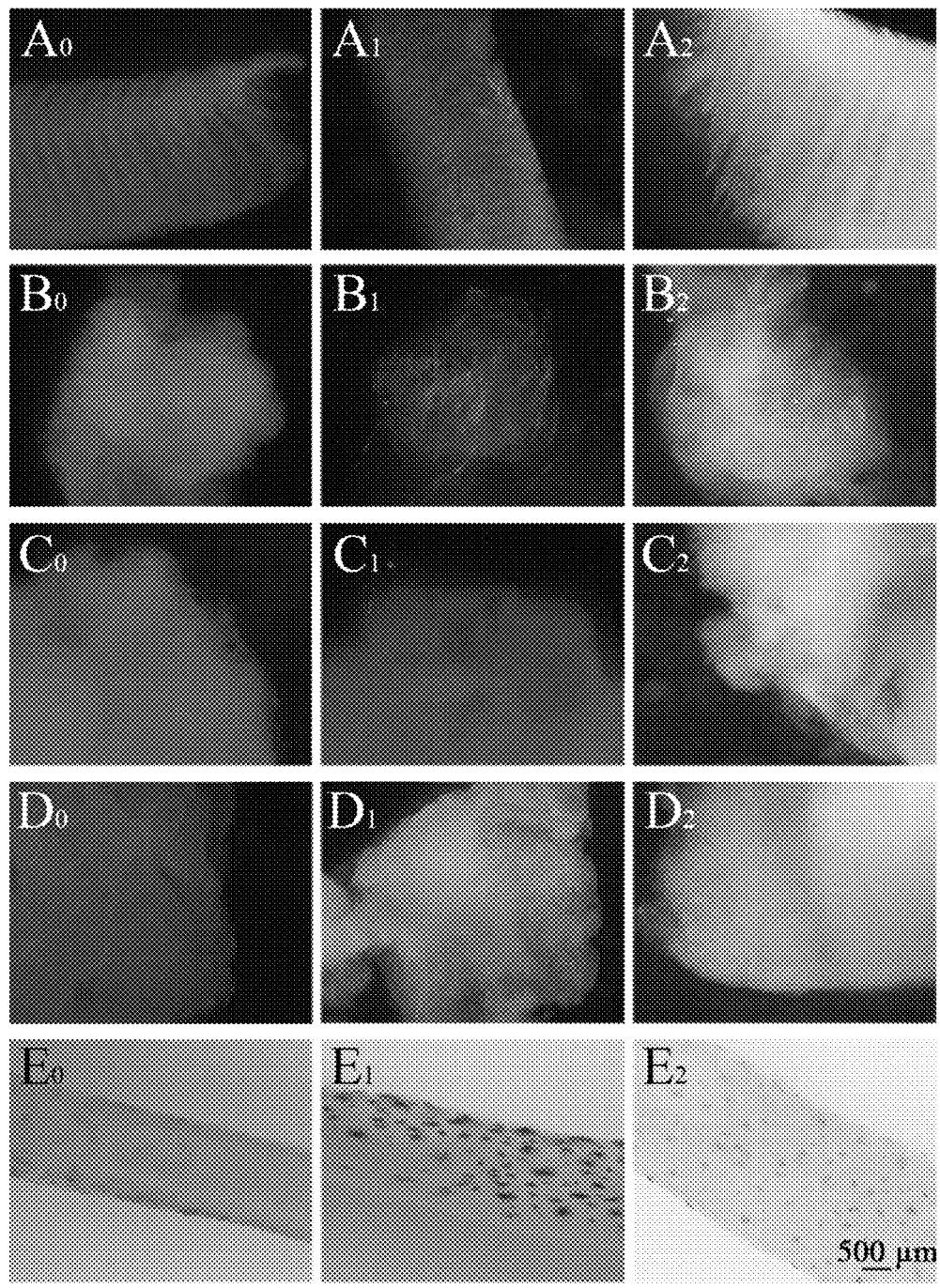
FIG. 10 shows the baculovirus Bacmid-GUS provided by the present invention cannot infect various adult shrimp tissues tested.

As shown in FIG. 10 (baculovirus Bacmid-GUS cannot infect tissues of an adult shrimp, where, A0 to E0 show GUS staining results of gill, Oka organ, heart, muscle and intestine tissues of a control shrimp intramuscularly injected with PBS; A1 to E1 show GUS staining results of gill, Oka organ, heart, muscle and intestine tissues of a shrimp intramuscularly injected with $3 \times 10^7$ TU of Bacmid-GUS virus; A2 to E2 show GUS staining results of gill, Oka organ, heart, muscle and intestine tissues of a shrimp intramuscularly injected with $1.5 \times 10^8$ TU of Bacmid-GUS virus; the infection is conducted by intramuscular injection, and the GUS expression is detected 120 h after virus infection; and scale bar: 500 m), no GUS gene expression is detected in gill, Oka organ, heart, muscle and intestine tissues of shrimps injected with baculovirus Bacmid-GUS at all dosages, indicating that the unmodified baculovirus Bacmid-GUS cannot effectively infect the above five shrimp tissues.

Figure 11:
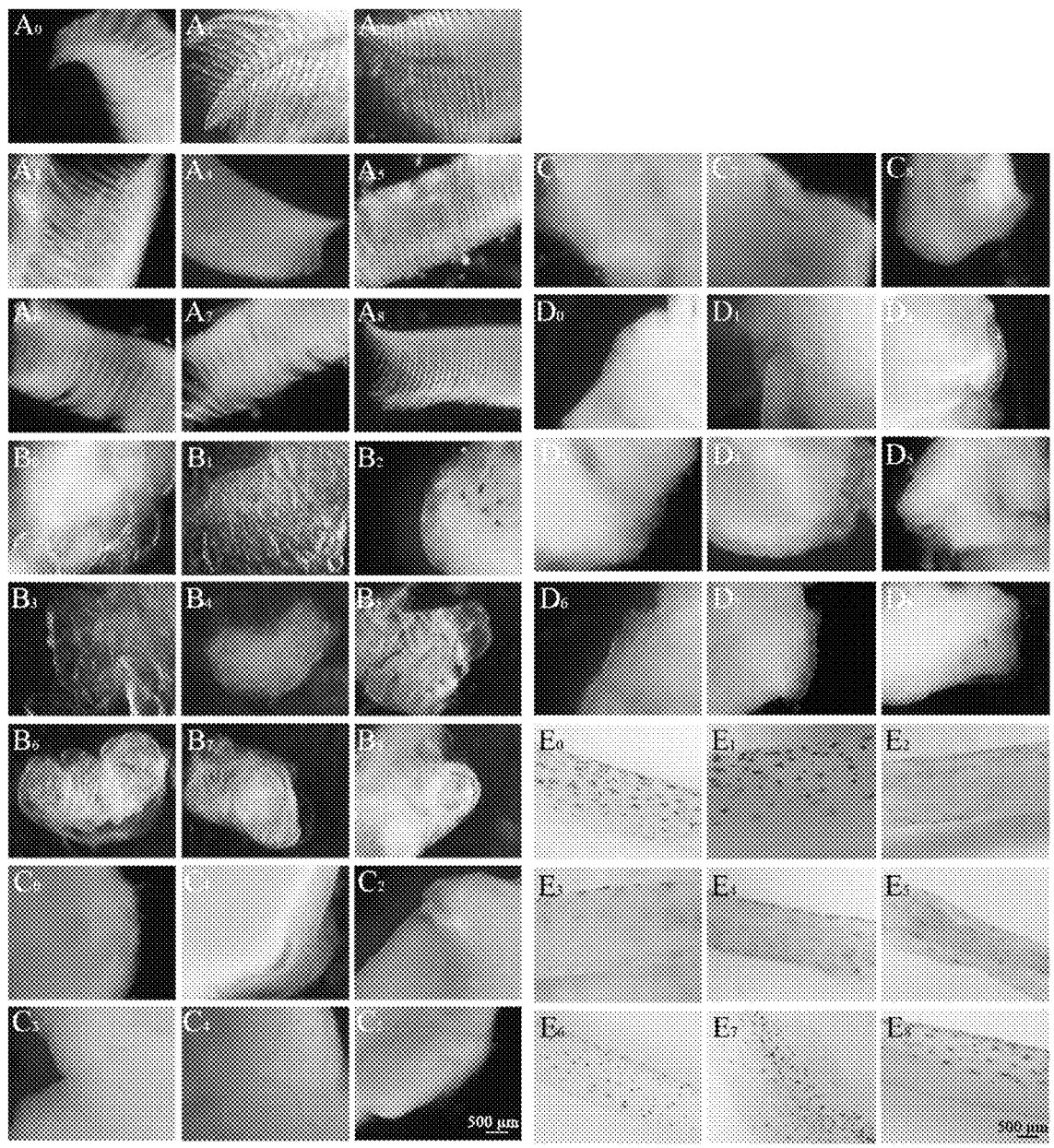
FIG. 11 shows that the pseudotyped baculovirus Bacmid-GUSNP28 provided by the present invention can efficiently infect gill, heart and intestine tissues of an adult shrimp.

However, as shown in FIG. 11 (pseudotyped baculovirus Bacmid-GUS/VP28 can efficiently infect gill, heart and intestine tissues of an adult shrimp, where, A0 to A8 show GUS staining results of shrimp gill tissues injected with 0 (PBS), $1.5 \times 10^4$, $1.5 \times 10^5$, $1.5 \times 10^6$, $1.5 \times 10^7$, $3.0 \times 10^7$, $1.5 \times 10^8$, $3.0 \times 10^8$ and $6.0 \times 10^8$ TU of Bacmid-GUS/VP28 pseudotyped baculovirus, respectively; B0 to B8, C0 to C8, D0 to D8 and E0 to E8 show GUS staining results of Oka organ, heart, muscle and intestine tissues, respectively; the infection is conducted by intramuscular injection, and the GUS expression is detected 120 h after virus infection; and scale bar=500 μm), GUS gene expression can be detected in gill and heart tissues of shrimps infected with pseudotyped baculovirus Bacmid-GUS/VP28 at all dosages, and at a dosage of $1.5 \times 10^7$ TU, the expression signal of GUS gene can also be detected in intestine tissues of all infected shrimps. It indicates that the introduction of VP28 envelope protein of the shrimp virus also significantly improves the tropism of pseudotyped baculovirus Bacmid-GUS/VP28 for an adult shrimp tissue, and the infection of the pseudotyped baculovirus is tissue-specific, targeting gill, heart and intestine tissues. However, GUS gene expression is not detected in all five tissues of a control shrimp intramuscularly injected with PBS, indicating that there is no significant background expression of GUS gene in adult shrimp tissues, and thus GUS gene can also be used for the gene transfer research on adult shrimps.

Figure 12:
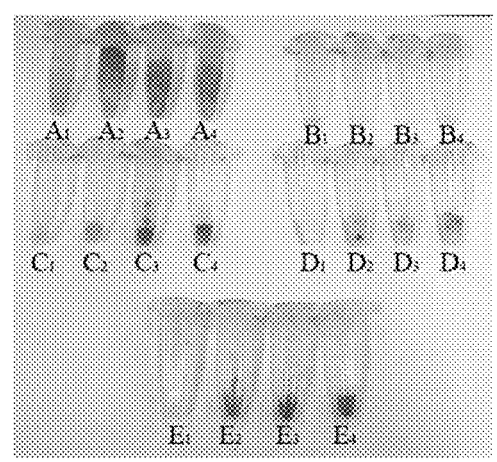
FIG. 12 shows the GUS expression results of the shrimp on days 1 to 4 after the infection of pseudotyped baculovirus Bacmid-GUS/VP28 provided by the present invention.

As shown in FIG. 12 (GUS expression results on days 1 to 4 after the infection of pseudotyped baculovirus Bacmid-GUS/VP28 in a shrimp, where, A1 to A4 show GUS staining results of shrimp gill issues on days 1, 2, 3 and 4 after the virus infection, respectively; B1 to B4, C1 to C4, D1 to D4 and E1 to E4 are the corresponding GUS staining results of shrimp Oka organ, heart, muscle and intestine tissues, respectively; the infection is conducted by intramuscular injection, and the infection dosage is $3 \times 10^8$ TU virus per shrimp), the infection and expression of pseudotyped baculovirus Bacmid-GUS/VP28 in adult shrimp tissues is time-dependent, and the GUS expression signal is intensified with the increase of infection time.

GUS staining was performed on adult shrimp tissues as follows: a GUS tissue staining solution was prepared in the dark just before use, with 1 mL of tissue staining solution including 830 μL of nuclease-free sterile water, 100 μL of 1 M sodium phosphate solution, 20 μL of 0.5 M EDTA-2Na, 10 μL of 10% TritonX-100, 20 μL of 50 mM potassium ferricyanide solution and 20 μL of 0.1 M X-Gluc solution (50 mg/mL); the GUS tissue staining solution was added to a centrifuge tube including a tissue, with the tissue being immersed; the centrifuge tube was incubated overnight in a 28° C. incubator; the centrifuge tube was taken out from the incubator, and the staining solution was carefully discarded; the tissue was picked up by a tweezer and placed in a small dish filled with PBS; and the tissue was observed under a stereomicroscope, and results were recorded by photographing.

In conclusion, the pseudotyped baculovirus gene transfer system constructed by the present invention can achieve an infection and expression efficiency up to 100% in adult shrimp tissues, significantly superior to the unmodified baculovirus gene transfer and expression system.

Moreover, the construction method of the present invention is also applicable to other envelope proteins of the WSSV, such as VP19, and envelope proteins of other shrimp viruses. The introduction of a different shrimp virus envelope protein into an insect baculovirus will result in a prepared pseudotyped baculovirus with a different tissue- and cell-specificity.

The above descriptions are merely preferred implementations of the present invention. It should be noted that a person of ordinary skill in the art may further make several improvements and modifications without departing from the principle of the present invention, but such improvements and modifications should be deemed as falling within the protection scope of the present invention.

What is claimed is:

1. A construction method of a pseudotyped insect baculovirus for shrimps based on a gene transfer system, comprising the following steps:
   1) constructing, with a Bac-to-Bac insect baculovirus expression system, an insect baculovirus recombinant plasmid comprising a foreign gene; and
   2) co-transfecting the insect baculovirus recombinant plasmid obtained in step 1) and an expression plasmid carrying shrimp virus envelope protein gene into an insect packaging cell to obtain a pseudotyped insect baculovirus for shrimps;
   wherein the gene transfer system for shrimps comprises a Bac-to-Bac insect baculovirus expression system, a shrimp virus envelope protein gene expression plasmid and an insect packaging cell;
   wherein the envelope protein gene in the shrimp virus envelope protein gene expression plasmid has a nucleotide sequence as shown in SEQ ID NO. 1.

2. The construction method of a pseudotyped insect baculovirus for shrimps based on the gene transfer system according to claim 1, wherein the shrimp virus envelope protein gene expression plasmid comprises the expression plasmid carrying shrimp white spot syndrome virus (WSSV) envelope protein gene.

3. A construction method of a pseudotyped insect baculovirus for shrimps based on the gene transfer system according to claim 1,
   wherein a framework vector for constructing the shrimp virus envelope protein gene expression plasmid comprises pcDNA3.1.

4. A construction method of a pseudotyped insect baculovirus for shrimps based on the gene transfer system according to claim 2,
   wherein a framework vector for constructing the shrimp virus envelope protein gene expression plasmid comprises pcDNA3.1.

* * * * *